United States Patent
Sponsel et al.

(10) Patent No.: US 6,415,173 B1
(45) Date of Patent: Jul. 2, 2002

(54) METHOD FOR ANALYZING THE OPTIC DISC FROM STEREO COLOR PHOTOGRAPHS USING VASCULAR LANDMARKS

(76) Inventors: William E. Sponsel, 19733 La Sierra, San Antonio, TX (US) 78256; Joseph T. Kavanaugh, 7207 Snowden Rd. Apartment 808B, San Antonio, TX (US) 78240

( * ) Notice: Subject to any disclaimer, the term of this patent is extended or adjusted under 35 U.S.C. 154(b) by 0 days.

(21) Appl. No.: 09/623,615

(22) PCT Filed: Mar. 5, 1999

(86) PCT No.: PCT/US99/05013
§ 371 (c)(1),
(2), (4) Date: Nov. 22, 2000

(87) PCT Pub. No.: WO99/44497
PCT Pub. Date: Sep. 10, 1999

Related U.S. Application Data

(60) Provisional application No. 60/077,068, filed on Mar. 6, 1998.

(51) Int. Cl.[7] .............................. A61B 3/10; A61B 5/00
(52) U.S. Cl. ...................... 600/407; 600/425; 600/558; 351/206
(58) Field of Search ................................ 351/205, 206; 600/407, 425, 473, 476, 558

(56) References Cited

U.S. PATENT DOCUMENTS

| | | | | |
|---|---|---|---|---|
| 5,868,134 A | * | 2/1999 | Sugiyama et al. | 600/300 |
| 6,030,079 A | * | 2/2000 | Torii | 351/205 |
| 6,134,341 A | * | 10/2000 | Kawamura et al. | 351/200 |
| 6,224,212 B1 | * | 5/2001 | Noda et al. | 351/206 |
| 6,276,799 B1 | * | 8/2001 | Van Saarloos et al. | 351/206 |

* cited by examiner

*Primary Examiner*—Ruth S. Smith
(74) *Attorney, Agent, or Firm*—Cox & Smith Incorporated

(57) ABSTRACT

A method for analyzing the optic disc from photographs using vascular landmarks. Monochromatic simultaneous stereo images of an eye are obtained. Reference points are marked on each disc margin. The position of a cup base is estimated and intermediate measurements of the data are tabulated.

1 Claim, 1 Drawing Sheet

METHOD FOR ANALYZING THE OPTIC DISC FROM STEREO COLOR PHOTOGRAPHS USING VASCULAR LANDMARKS

This application claims priority from Provisional application Ser. No. 60/077,068, filed Mar. 6, 1998.

BACKGROUND OF THE INVENTION

This invention relates to a method and apparatus for analyzing the optic disc; and more particularly, a method for health analysis of the eye by the use of stereo photographs.

In glaucoma, optic nerve head changes precede functional visual field loss. Current clinical estimates of cup to disc ratios have been shown to be unreliable. The standard for objectively documenting optic nerve head changes is by stereo photography. Jonas et al has shown the pattern of neuroretinal rim loss occurs in sectoral sequence:

(inf.temp.>sup.temp.>temp.>inf.nasal>sup.nasal). Despite this, vertical and horizontal indices are still universally used when assessing stereo photographs.

Studies confirm that standard measures of cup/disc ratio are subject to extraordinarily high degrees of intra- and interobserver variability.

SUMMARY OF THE INVENTION

A method for analyzing the optic disc from photographs using vascular landmarks may be achieved by acquiring monochromatic or color simultaneous stereo images of the ocular fundus. Nasal, superotemporal, and inferotemporal reference points are marked on each disc margin with a mouse cursor. The position of the cup base along each of the two axes subtended between the nasal reference point and two temporal disc rim points are estimated. Alternatively, a central reference point within the disc may provide the axis for a triad of lines, one to a nasal landmark, and two as previously described toward the superotemporal and inferotemporal disc perimeter. Placement is intended to maximize as fully as possible the avascular alleyways and to subtend maximally the extant or anticipated zones of superior and inferior cupping, avoiding vasculature. The Chevron Ratio is the summed length of axes subtending the cupped portion of the disc over the sum of the axes to the disc margin. Reproducibility studies have demonstrated that computer-assisted measurements are twice as accurate as manually derived measurements with this technique, and take only seconds as opposed to minutes to calculate. Either manual or computerized Chevron ratios provide data vastly more reproducible than that typically attained with standard estimates of vertical or horizontal cup-to-disc ratios in common clinical use. A Discam (Marcher Enterprises, Hereford, UK) digital image camera and computer system has been programmed to provide intermediate measurements along each axis. These are initially entered by adjustment of the length, angle, and position of computer-generated angular lines from initially randomized cursor settings on screen over one of the stereo images. Cupping estimates are then entered along the assigned axes similarly, and may be re-entered along the very same axes during subsequent patient visits. The current system is therefore semi-automated, with the reference axes automatically generated on each successive stereo photograph in a patient series, but requiring the identification of the cup base by stereoanalysis of the images by the clinician along the constrained axes using a mouse at each visit. Fully automated systems are under development, pending the compilation of massed data on numerous discs from many clinicians so that the computer-assisted estimates of cupping will emulate those empirically determined by standard clinical acumen.

DESCRIPTION OF THE PREFERRED EMBODIMENT

Figure 1:
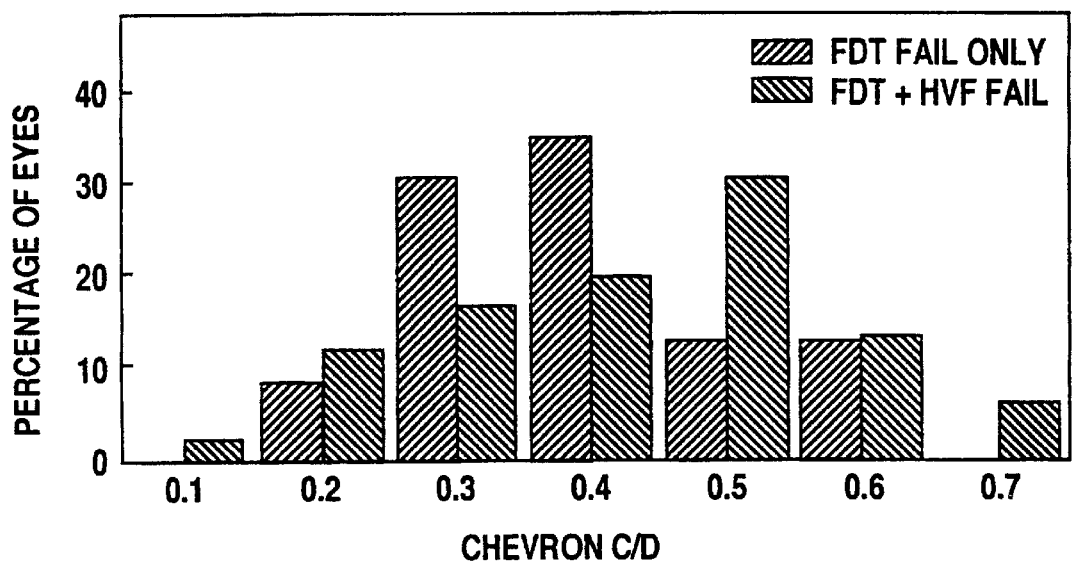
FIG. 1 illustrates a graph Discam-Chevron c/d ratio for the pathologic fellow eyes of patients in Example 4.

The present invention demonstrates that measurements of the nasal to superotemporal and nasal to inferotemporal axes, areas known to be preferentially damaged in glaucoma, can be reproducibly measured manually from stereo photographs using retinal vessels and the neuroretinal rim as landmarks. This methodology, once integrated into a computerized stereo-image analysis system, can generate highly reproducible data of much greater clinical relevance than is typically afforded by standard optic disc measurement techniques. Early evidence of pathologic progression using this method may be more evident than that obtained using scanning laser imaging methods costing many times more, because these latter systems tend to rely on realigning 3-dimensional data, which imposes severe processing and analysis limitations. The simplicity of the Chevron technique, its utilization of a 2-dimensional ratio not subject to magnification or rotation, and most importantly, its focus upon the epidemiologically-demonstrated cross-sectional disc axes of greatest pathologic relevance combine to make this novel method an easily-understood, reproducible, and clinically useful measurement technique for the diagnosis and treatment of glaucoma (a disease which accounts for 13% of adult blindness in North America).

Computer-assisted methodology also allows the use of nonvascular landmarks, and has verified that the very best measurements can be obtained from completely avascular axes running from the nasal to the inferotemporal and superotemporal rims of the optic nerve head.

EXAMPLE 1

Three observers performed measurements on each of 20 stereo pairs of disc photos. Three measurements from a nasal reference point to the inferotemporal disc rim landmark and to the supertemporal disc rim landmark were performed on separate occasions using a 100 micron graticule. Measurements along these axes to the cup base were performed on three different occasions for each stereo pair by each observer.

Measurements from the nasal reference point to the superotemporal and inferotemporal vascular landmarks were highly reproducible and consistent between observers (R=0.974). Measurements of the cupping along the nasal inferotemporal and nasal superotemporal axes were also highly reproducible (R=0.93). These results were then recorded as a ratio similar to the universal cup/disc measurements but instead incorporate the nasal reference point (not the nasal disc margin) and the measurement taken along the superotemporal or the inferotemporal axes. The Chevron ratio is a reproducible method for analyzing glaucomatous optic neuropathy by using defined vascular or other trigonometric landmarks and the depressed temporal border of the cup.

EXAMPLE 2

The method involves the stereoscopic use of a mm graticule to obtain cumulative inferotemporal-to-nasal-tosuperotemporal cup-to-disc ratios and has been shown to have low intra- and interobserver variability. Disc-centered stereo fundus slides taken at baseline and follow-up were analyzed in 17 glaucomatous eyes by 5 glaucoma surgeons, in a masked manner. The follow-up period was 24±10 months.

Although the Chevron ratio increased from only 0.627±0.089 to 0.707±0.101 (by 13%) there was statistical affirmation that the changes detected were highly significant for each individual observer and for the grand average (p=0.0012). There were no significant differences between observers.

This manual method for assessing the Chevron Ratio is readily capable of detecting progression of disc cupping of 130 microns. Analyzing stereo fundus slides using this manual method is tedious and time consuming, however. Image acquisition and Chevron analysis can be performed economically and very rapidly using digital imaging, with even greater accuracy.

EXAMPLE 3

Monochromatic simultaneous stereo images (2×512K pixel) were acquired from 23 glaucomatous eyes, and analyzed by 4 glaucoma surgeons in a masked manner. One surgeon marked nasal, superotemporal, and inferotemporal reference points on each disc margin with a mouse cursor, and all 4 independently estimated the position of the cup base along each of the two axes subtended between the nasal reference point and the 2 temporal disc rim landmarks. The Discam (Marcher Enterprises, Hereford, UK) computer provided immediate measurements along each axis, which were tabulated by a neutral observer-who randomized the cursor settings between each reading.

Chevron Ratios ranged uniformly from 0.3–0.8 among the 23 eyes. The Coefficient of variation among the 4 observers fro the 23 sets of disc measurements was 8.5%, (SD equating to 77 microns, assuming average disc diameter of 1.5 mm). These reproducibility data are twice as precise as those obtained by the same experts in time-consuming, tedious measurements of transilluminated color transparencies, a technique shown capable of detecting small changes in disc morphology with very high confidence. The Discam, which acquires and analyzes optic disc images in far less than the time required for the awkward and painstaking tabulation of comparable data from stereo disc transparencies, is capable of providing detailed and clinically relevant data at low expense for clinical documentation and monitoring of glaucomatous neruopathology.

EXAMPLE 4

To determine the distribution of the Chevron ratio cup to disc (c/d) values among eyes failing the Frequency Doubling Technology (FDT) visual screening tests, 574 people (421 males and 153 females) participated in a voluntary health screening over a 3-day period. Participants underwent a FDT C-20-1 screening test in both eyes. Participants missing two or more stimuli in either eye with FDT underwent Humphrey SITA—fast 24-2 perimetry and Discam stereo disc analysis.

Forty-eight subjects (96 eyes) completed all three tests, having shown two or more defects on the FDT in one or both eyes. Pathologic Humphrey fields were found to exist in sixty-six of the ninety-six eyes. The Discam-Chevron c/d ratios for the pathologic and nonpathologic fellow eyes were distributed as shown in FIG. 1.

FIG. 1 illustrates the relationship between Chevron cup/disc ratios on subpopulations failing a visual function screening test (FDT fail only; light bars) and the subset of that population failing both the screening test and a standard clinical perimetry assessment with the Humphrey Visual Field 24-2 (FDT+HVF fail; dark bars). The distribution of Chevron c/d values is significantly higher among the eyes with the more strict visual function failure criteria, demonstrating the clinicopathologic correlation of optic nerve and visual field findings using this technique. The Chevron c/d ratios tend to be lower ratios than those typically obtained among pathologic eyes using vertical or horizontal c/d measurements, since the Chevron axes tend to subtend through both cupped and non-cupped regions. This latter feature enhances the utility of the Chevron method for monitoring change over time, since a patient is far less likely to become "cupped-out" early on (which tends to truncate traditional horizontal and vertical c/d ratios in the 0.8–0.9 range and thereby limit their utility in monitoring disease progression).

Thus, an association between the visual field damage and Chevron c/d ratios exists among the test population.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

We claim:

1. A method for analyzing the optic disc from photographs using vascular landmarks comprising:

acquiring monochromatic simultaneous stereo images of an eye on a disc;

marking nasal, superotemporal and inferotemporal reference points on each said disc margin;

estimating the position of a cup base along each of two axes subtended between said nasal reference point and two temporal disc rim points;

obtaining intermediate measurements along each said axis; and tabulating data obtained.

* * * * *